United States Patent [19]
McMeekin et al.

[11] Patent Number: 4,874,940
[45] Date of Patent: Oct. 17, 1989

[54] METHOD AND APPARATUS FOR INSPECTION OF A TRANSPARENT CONTAINER

[75] Inventors: James H. McMeekin, Brockway; Alan E. Lerch; Ronald S. Chollock, both of DuBois; James F. Wesdock, Reynoldsville, all of Pa.

[73] Assignee: Brockway, Inc. (N.Y.), Jacksonville, Fla.

[21] Appl. No.: 141,844

[22] Filed: Jan. 11, 1988

[51] Int. Cl.⁴ ............... G01N 9/04; G06M 7/00; H01J 40/14
[52] U.S. Cl. .................. 250/223 B; 356/240
[58] Field of Search ............ 250/223 B, 563; 356/240, 239; 209/526

[56] References Cited
U.S. PATENT DOCUMENTS

| | | |
|---|---|---|
| 3,101,848 | 3/1961 | Uhling . |
| 3,249,224 | 5/1966 | Uhlig . |
| 3,262,561 | 7/1966 | Sorbie . |
| 3,356,853 | 12/1967 | Rottman .................. 250/223 B |
| 3,557,950 | 1/1971 | Powers . |
| 3,746,165 | 7/1973 | Ford et al. . |
| 3,848,742 | 11/1974 | Krenmayr . |
| 4,083,637 | 4/1978 | Ellinger et al. .............. 250/223 B |
| 4,335,960 | 6/1982 | Ashcroft et al. ............. 250/223 B |
| 4,435,641 | 3/1984 | Hajime ..................... 250/223 B |
| 4,448,526 | 5/1984 | Miyazawa ................... 250/223 B |
| 4,655,349 | 4/1987 | Joseph et al. . |
| 4,691,231 | 9/1987 | Fitzmorris et al. . |

Primary Examiner—David C. Nelms
Assistant Examiner—Eric F. Chatmon
Attorney, Agent, or Firm—Burns, Doane, Swecker & Mathis

[57] ABSTRACT

A method and apparatus for inspecting the bottom of a transparent container for defective conditions, such as internal stuck glass, internal loose glass or foreign material. The container is provided in an inspection zone and a linearly extending line of light from a light source is focused to pass through the container bottom with the line of light extending the length of the inspection zone and hence the length of the container bottom. The linearly extending line of light enters the container through the exterior surface of the container bottom. The intensity of the light reflected from defects in or within the container and through the container side wall at a predetermined angle is detected. The detected intensity of the reflected light is compared with a predetermined threshold value that provides a measure of the acceptability of the container.

40 Claims, 6 Drawing Sheets

METHOD AND APPARATUS FOR INSPECTION OF A TRANSPARENT CONTAINER

BACKGROUND OF THE INVENTION

The present invention relates to a method and apparatus for automatically detecting the presence of defects in transparent containers, particularly those produced from glass. In particular, the present invention is directed to the automatic detection of defects located in or near the bottom of a transparent container.

Transparent containers, such as glass bottles and the like, are subject to a number of different types of defective conditions. Such defective conditions, which may be present in the bottom of the container or the lower portion of the side wall, could include fissures, split heels, split bottoms, internal stuck glass, internal loose glass, external stuck glass, impacted baffles, foreign objects or materials, tears, blisters, and the like.

The containers must either be individually inspected by human inspectors to reject those having a defect condition, or inspected by any of various types of known automatic systems that have been proposed for inspecting various defects. Examples of inspection systems relating to container bottom inspection include those disclosed in U.S. Pat. Nos. 3,557,950 and 3,101,848. In the systems disclosed in these patents, each container is stopped in its path of travel and rotated while a spot on it is illuminated with a beam of light. In another type of inspection system disclosed in U.S. Pat. No. 3,746,165, the container continuously moves through an inspection system while its entire bottom is illuminated with diffused light.

In another known type of inspection system, a plurality of containers rotate and continuously move through an inspection zone. A line of light from a light source is directed at a mirror which reflects the light through the side wall toward and across the bottom of the containers to be inspected. The reflected light which passes through the bottom of the container can again be reflected by defects or objects in or on the bottom of the container. This additionally reflected light can then be detected by a line scan camera.

While these known systems are capable of detecting at least some defects in or associated with the bottom of a transparent container, it is desirable to provide an inspection system which provides greater reliability and efficiency in the detection of defects, particularly those defective conditions associated with the interior bottom surface of the container. Such defects would include, for example, internal stuck glass, internal loose glass or foreign material.

OBJECTS AND BRIEF STATEMENT OF THE INVENTION

Accordingly, it is a general objective of the present invention to provide a novel method and apparatus for automatically detecting defects in transparent containers, particularly for detecting defects in or associated with the bottom of a transparent container.

It is a more specific object of the invention to provide such an apparatus and method that is capable of detecting various types of defective conditions that are commonly encountered in or associated with the interior bottom surface of a container with enhanced reliability and efficiency.

Briefly, according to the present invention, these and other objectives are achieved by means of a method and apparatus for inspection of a transparent container in which light from a source is focused into a linearly extending line of light which passes through the bottom of the container. The light enters the container through the exterior surface of its bottom. The line formed by the focussed light is longer than the width of the container, so that it extends across the bottom of the container.

The method for inspection further includes detecting the intensity of the light which passes through the interior surface of the bottom and is reflected by defects through the container side wall at a predetermined angle. The detected intensity of the reflected light generates an electrical signal which is compared with a predetermined threshold value, to provide a measure of the acceptability of the container.

The apparatus for inspection of a container includes a means for supporting at least one container in an inspection zone. The apparatus further includes a light source which provides a focussed line of light that passes through a portion of the container bottom from its exterior surface. The line of light from the light source extends the length of the inspection zone and thus along the length of the container bottom. The apparatus further includes means for detecting the intensity of light which has passed through the container bottom and has been reflected, due to defects, through the side wall at a predetermined angle. Also, the apparatus includes means for comparing an electrical signal related to the detected intensity of the reflected light with a predetermined threshold value, to provide a measure of the acceptability of the transparent container.

According to the invention, it is desirable to rotate the container in the inspection zone to permit inspection of the entire bottom. It is further desirable to move the container through the length of the inspection zone while rotating the container to permit continuous inspection of the bottom. In this regard, it is further desirable to space and continuously move more than one container through the inspection zone to permit simultaneous inspection of multiple containers.

Further features and advantages of the invention are explained in greater detail hereinafter with reference to a preferred form of the invention illustrated in the accompanying drawings.

DESCRIPTION OF THE ILLUSTRATED EMBODIMENT

In the following description of preferred embodiments of the invention, particular reference is made to the inspection of glass containers in order to facilitate an understanding of the invention. However, it will be appreciated that the invention is not limited to this specific application. Rather, the invention may be applicable to containers made from various types of other transparent materials. For convenience, similar elements in the various figures are identified with the same numerical identification.

Figure 1:
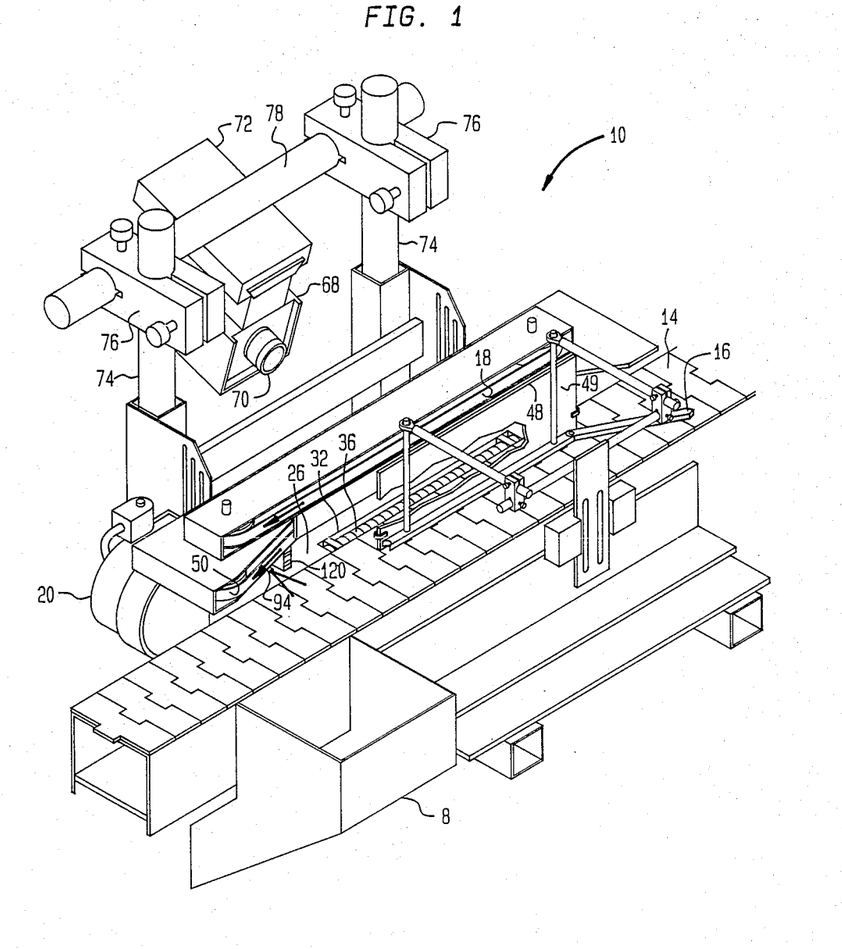
FIG. 1 is a perspective view of an apparatus incorporating the present invention.
Figure 2:
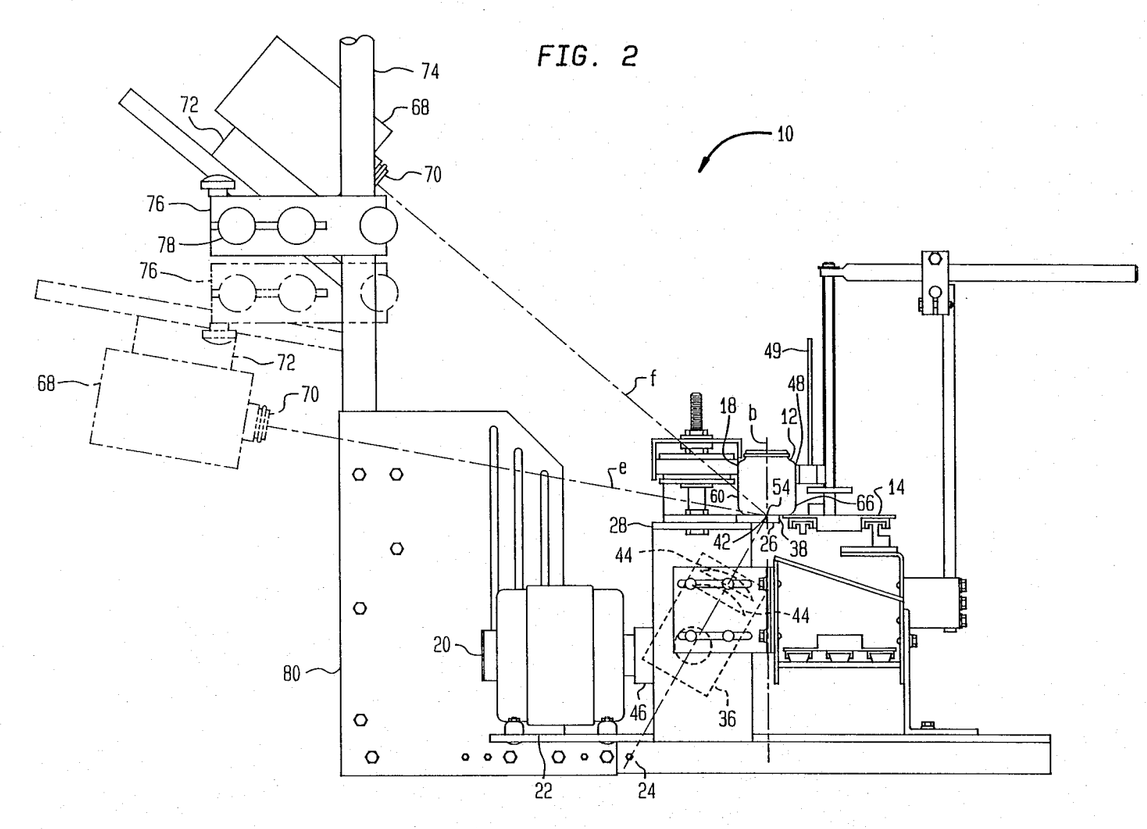
FIG. 2 is a schematic drawing in a partially sectioned side view illustrating an apparatus for implementing the present invention.
Figure 3:
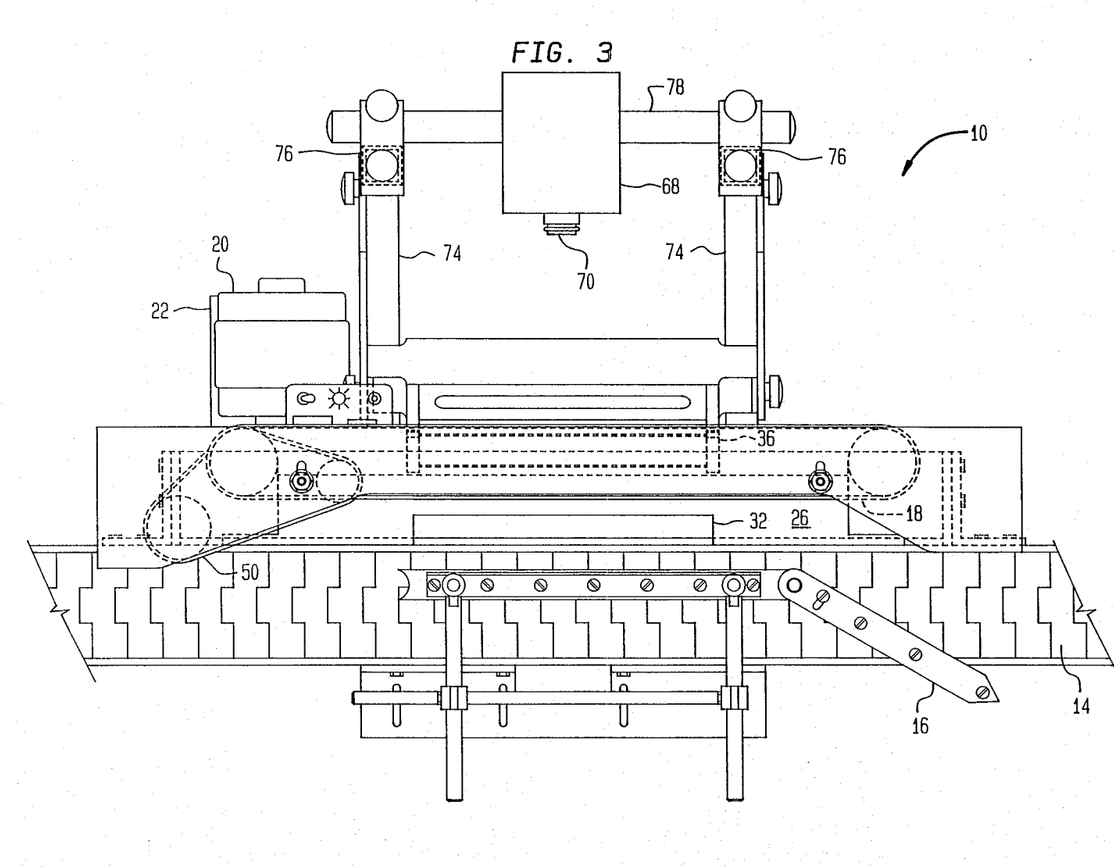
FIG. 3 is a top view of the apparatus illustrated in FIG. 2.

Referring to FIGS. 1 through 3, there is illustrated an inspection device 10 where transparent containers 12, such as glass containers, are presented by means of a continuously moving conveyor 14, such as a table-top chain conveyor. In the illustrated embodiment, the containers 12 are diverted from the conveyor 14 into the inspection device 10 by a diverting strip 16.

The containers 12 are moved through the inspection device 10 by a suitable means, such as a drive belt 18 connected to a drive motor 20 which powers the drive belt 18. The drive motor 20 is suitably supported on the inspection device 10, such as on a motor mounting plate 22 which is attached to a frame member 24. Preferably, the motor 20 is an AC synchronous motor to provide a constant belt speed.

Figure 4:
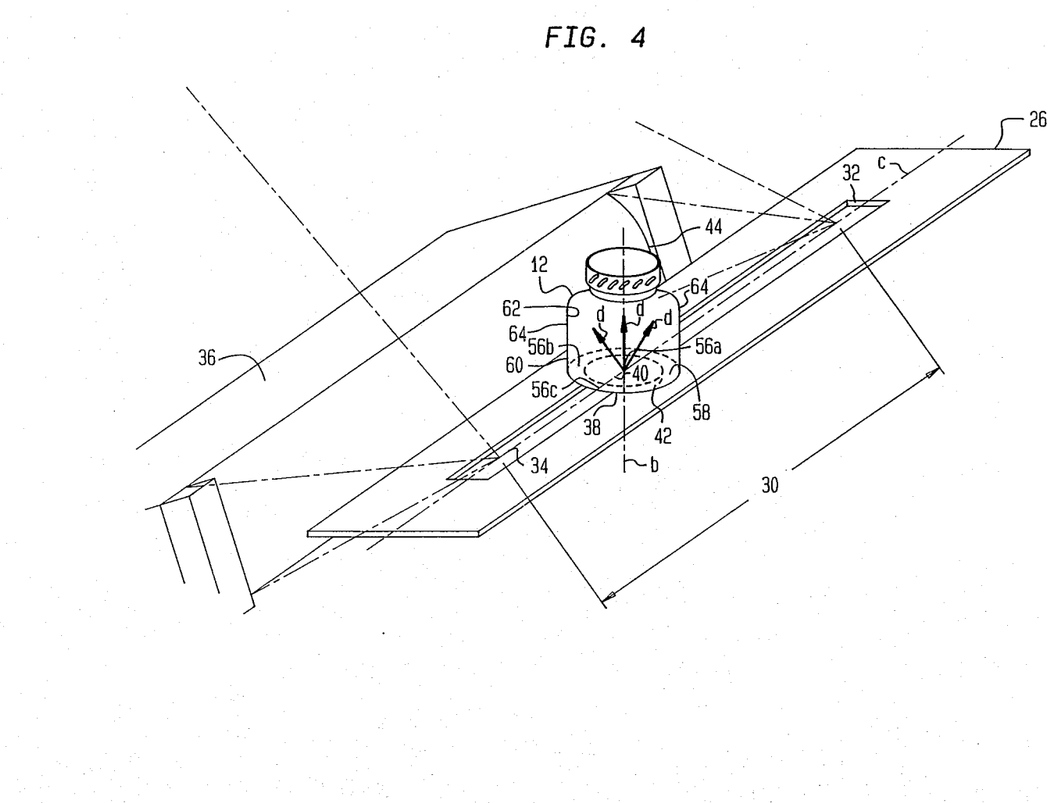
FIG. 4 is a perspective view of a transparent container in an inspection zone on a supporting member to illustrate the focusing and reflecting of the light from the light source in accordance with the present invention.

The drive belt 18 moves the container 12 onto a supporting member 26, such as a wear strip attached to a mounting plate 28. The supporting member 26 has a generally rectangular opening 32 which defines an inspection zone 30 and is adapted to pass a linearly extending line of light 34 (illustrated more clearly in FIG. 4) from a light source 36. The line of light 34 extends in the direction of travel of the containers through the inspection zone 30 and is focused in the area of the opening 32 where typically the center of the bottom of the containers 12 will pass. As illustrated in FIG. 4, the line of light 34 enters the container 12 through the exterior surface 42 of its bottom 38 and extends the length of the inspection zone.

Figure 5:
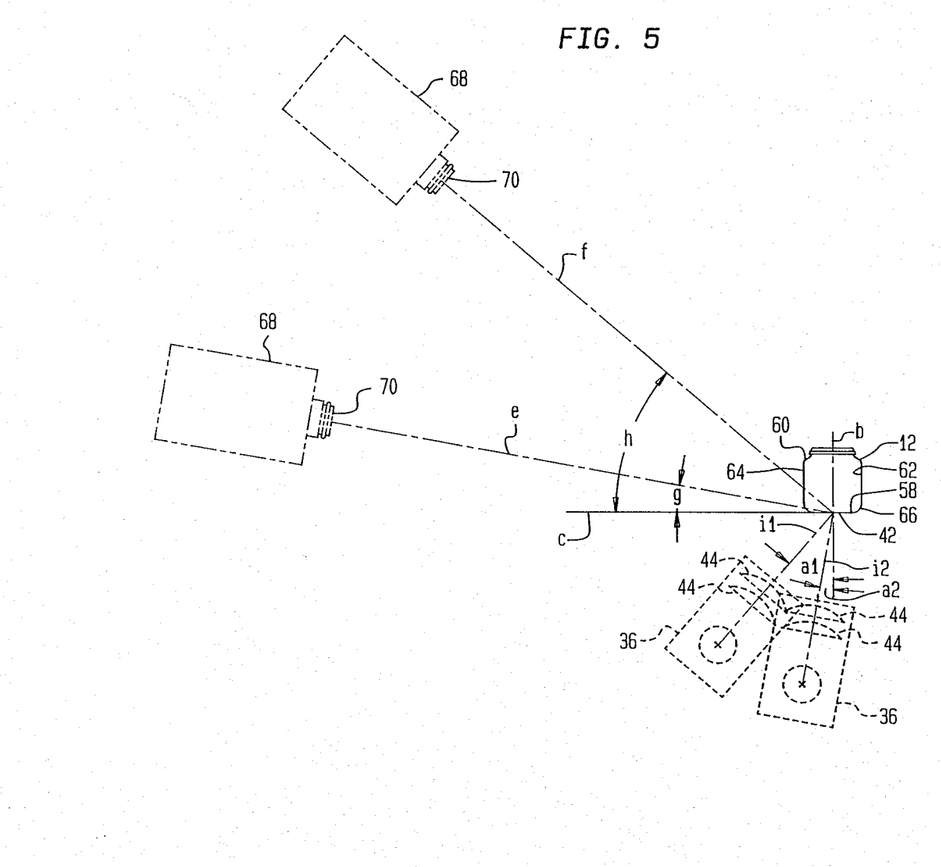
FIG. 5 is a further illustration of the principle of the present invention.

The light source 36 could be, for example, a tubular quartz infrared heat lamp of sufficient wattage which, typically for the inspection of glass containers, is 1000 watts. The light source includes a means to focus the light such as a lens arrangement 44 which desirably includes a cylindrical lens or lenses, as best shown in FIGS. 2, 4 and 5.

It is desirable to rotate the transparent containers 12 in the inspection zone 30 through a predetermined number of degrees to ensure that the line of light sufficiently crosses the container bottom 38 to permit inspection of a corresponding portion of that bottom. In this regard, the container should be rotated through at least 180 degrees, and more preferably 360 degrees, as it traverses the length of the inspection zone 30 to permit the inspection of the entire bottom.

With reference to FIG. 2 in particular, a means for rotating the transparent containers 12 in the inspection zone 30 is provided by the drive belt 18 and a roll strip 48 mounted to a back plate 49 in the inspection device 10. The back plate 49 can also serve as a light shield. The containers 12 engage the drive belt 18 and rotate against the roll strip as they move through the inspection zone 30. It is desirable that the inspection zone be of sufficient length so that the largest diameter of containers to be inspected can rotate through 360 degrees. Typically, the length of the inspection zone 30 can be in a range of from about 6 to 11 inches.

A portion of conveyor 14 may assist in moving the containers 12 into and out of the inspection zone 30. Also, a means for moving the containers as they leave the inspection zone 30 is illustrated by an outfeed belt 50 (FIGS. 1 and 3) which is suitably driven by the drive motor 20.

With this arrangement, it is possible to simultaneously and continuously inspect a plurality of containers 12 as they move through the inspection zone 30. Further, since the line of light extends throughout the length of the inspection zone 30, such simultaneous, continuous inspection of the bottom of a plurality of containers 12 is provided without the need to stop and rotate each container. To ensure adequate spacing of the containers in the inspection zone and thereby facilitate such continuous inspection, it is desirable that the speed of the containers 12 through the inspection zone 30 be slightly faster than the speed of the conveyor 14. Preferably, the speed of the containers through the inspection station should be on the order of about 10 to 20 percent faster than the speed of conveyor 14.

Referring particularly to FIG. 5, it is preferable that the linearly extending line of light 34 enter the exterior surface 42 of the container bottom at a preselected angle a. This preselected angle a is measured from a centrally extending plane b located in inspection zone 30 perpendicular to a plane c, which plane c is defined by the surface of the member 26 which supports the container whose bottom 38 is to be inspected. Typically, the plane c will be horizontal and the plane b will be vertical. It is desirable that the centrally extending plane b pass through the central portion of the container bottom 38, so that for a circular container, for example, the line of light extends along its diameter.

It is further preferred that the angle a be selected to promote optimum light reflection from one or more defective conditions present in or associated with the container bottom 38, such as internal stuck glass, internal loose glass, foreign objects or materials, fissures, or cracks, for example. FIG. 4 illustrates an example of a defective condition, i.e., the presence of pieces of glass 56a, 56b and 56c on the interior surface 58 of the bottom. Light reflected from the pieces of glass 56 is illustrated by the arrows d in FIG. 4.

The preselected angle a that is chosen to maximize light reflection from a defect is typically dependent on various factors, such as the type of container being inspected and the particular defects to be detected. To achieve maximum light reflection from defective conditions present in or associated with the container bottom 38 it is preferred that the preselected angle a be in a range of from about 15 degrees to about 45 degrees, with angles of 15 degrees, 30 degrees and 45 degrees being most preferred within that range. Two alternative preselected angles a1 and a2 are illustrated in FIG. 5 for the line of light 34 from the light source 36, with the light source 36 being shown in FIG. 5 in two possible positions corresponding to the preselected angles a1 and a2. The central axis of the incident beam of light from the light source 36 is illustrated by the letter i in FIG. 2 and the letters i1 and i2 in FIG. 5 corresponding to the preselected angles a1 and a2. This beam is focused so that the light rays in the beam converge in the vicinity of the bottom of the container, and thus the intensity of the beam is at a maximum in the area of primary interest with respect to the detection of defects. In other words, the beam is focussed on or near the plane c, to thereby provide the line of light which traverses the bottom of the container. In this regard, it is not necessary that the beam be focussed to a precise point. Rather, the focal area of the beam can have some measurable depth to it, to thereby account for containers which may have different respective amounts of curvature in their bottoms.

If the bottom of the container does not contain any defects, light will emerge from its interior surface and continue along a path that is in the general direction of the incident axis i. However, if the bottom of the container contains a defect, such as the pieces of glass 56a, b or c illustrated in FIG. 4, the light could be reflected in all directions but most of it will emerge at a significant angle. More particularly, the reflected light passing through the container side wall 60 as a result of defects in or on the bottom surface is primarily directed at a predetermined angle or angles. In accordance with the invention, the intensity of the light is detected at these angles. These angles are selectable to promote receiving maximum light as a result of the defective condition or conditions in the container 12 for which inspection is desired. The path of the reflected light to be detected is illustrated in FIGS. 2 and 5 by the letters e and f. This reflected light is detected at one or both of two predetermined angles g and h, respectively. It is preferred that the predetermined angles be in a range of about 10 degrees to about 40 degrees relative to the horizontal plane c.

The present invention has an advantage over known methods of inspection of the bottom of a container. Passing the line of light 34 through the container bottom 38 over its length and detecting the reflected light over that entire length at a predetermined angle promotes a higher degree of efficiency and reliability in the detection of defective conditions, such as internal stuck glass, internal loose glass, or foreign materials. Such enhanced reliability is achieved in that there is less likelihood of any interference with the reflected light from, for example, lettering, patterns, or the like which are typically present on the exterior surface 42.

A further advantage is that it is also possible to detect a defective condition which may exist in the lower portion 66 of the side wall 60 of a container 12. The lower portion 66 of the container side wall 60 which can be inspected varies according to the type of container to be inspected, although typically up to about one-half inch of the lower portion 66 of the side wall 60 that extends above the bottom 38 may be inspected.

Referring to FIGS. 1, 2, 3 and 5, a means for detecting the intensity of the reflected light which is passed through the container side wall 60, after the line of light 34 has passed through the bottom is illustrated. The means for detecting the intensity of the reflected light preferably comprises a line scan camera 68 whose field of view corresponds to the length of the inspection zone. The line scan camera 68 desirably includes an adjustable aperture and a lens 70 for limiting the amount of reflected light to a suitable range and focussing it onto a suitable detector within the camera 68, such as a linear photodiode array. The lens 70 of the camera 68 is desirably focused so that its front focal point coincides in space with the focused line of light 34. As a defective condition present in the bottom 38 of the container meets the line of light 34, the surfaces of the defect glow and/or provide mirror-like surfaces and reflect light into the optical path of the line scan camera 68.

It is possible to provide for more than one line scan camera to detect the reflected light at more than one predetermined angle. FIG. 5, for example, illustrates two such cameras 68. One of the cameras 68 is positioned to accept the reflected light f at the predetermined angle h while the other camera 68 is positioned to accept the reflected light e at the predetermined angle g. Alternatively, it is possible to provide a single camera 68 that can be adjustably positioned at a plurality of locations and angles in the inspection device 10, such as illustrated in FIG. 2. The number of cameras that are employed and the angles at which they are positioned will be determined by the number and types of defects that the container is to be inspected for. Thus, one camera at an angle h of 40 degrees might be used to detect stuck or loose glass, and another camera at an angle g of 10 degrees can be used to detect fissures and cracks in the bottom and lower side wall of the container.

As illustrated in FIGS. 1 through 3, the camera 68 is suitably mounted to a camera mount or detector mounting assembly 72 in the area of the inspection device 10. The detector mounting assembly 72 is adjustably mounted on a pair of camera mounting tubes 74 by means of a pair of adjustment members 76 which permit vertical positioning of the camera. Rotational positioning of the camera about a horizontal axis, as well as horizontal positioning along the axis, is provided by a camera mount support member 78 to which the detector mounting assembly 72 is suitably connected.

In the embodiment of the inspection device 10 illustrated in the figures, the camera mounting tubes 74 and the camera mount support member 78 are generally cylindrical members which are adapted to be received in generally cylindrical openings within the adjustment members 76. The adjustment members 76 can be any suitable means capable of adjustably mounting to the camera mounting tubes 74 and to the camera mount support member 78, such as a dovetail slide and clamping bar having adjustment knobs. The camera mounting tubes 74 are mounted in the inspection device 10 by elbow members 80 which are attached to the frame member 24 as illustrated in FIG. 2.

The reflected light, such as reflected light along the path e or f, is focused by the lens 70 onto the linear photodiode array within the camera 68. The reflected light received by the photodiodes is converted to an electrical signal, which is then amplified to a suitable working voltage level. The magnitude of this signal is compared to a threshold value. This threshold value is a user-settable reference that is dependent upon the defective condition to be detected.

Figure 6:
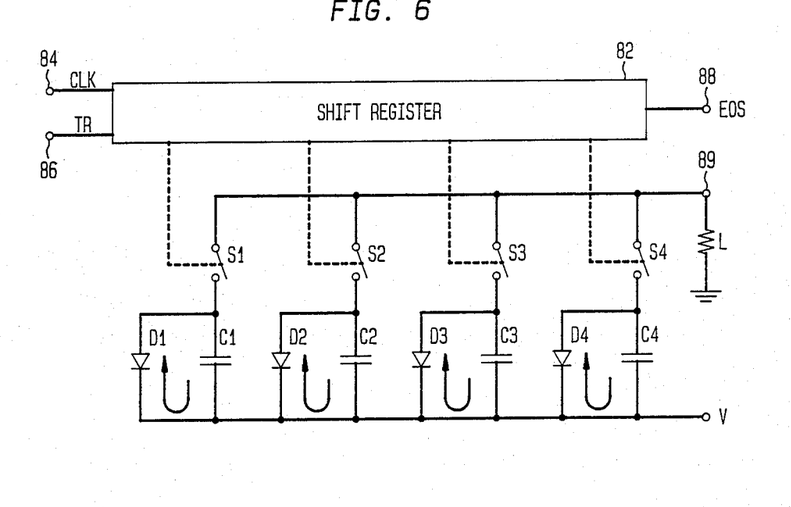
FIG. 6 is a simplified array diagram for a linear photodiode light detection array for use in the present invention.

The operation of the line scan camera to detect the reflected light intensity is illustrated in FIG. 6. The lens 70 is typically a standard television camera lens to focus the reflected light onto the detector array in the camera 68. A portion of the array is represented by the diodes D1-D4 illustrated in FIG. 6. Four switches S1-S4 are respectively connected in series with capacitors four C1-C4. Typically, each switch is controlled by circuitry, such as a shift register 82 having array start and clock signal inputs respectively applied at terminals 86 and 84. Typically, as the start pulse is shifted through the register, it actuates the switches S1-S4 in sequence. After the last switch S4 has been closed and opened, the start pulse is shifted to an output terminal 88 to provide an end of scan (EOS) signal. The output signal from the photodiode detector array is obtained at the output terminal 89. Typically, plural shift registers 82 may be utilized with each shift register connected to a portion of the photodiodes in the array. Where two shift registers are utilized, two output terminals 89 would be connected together and typically to a current amplifier which acts as the load resistor and amplifies the current pulses through it.

To detect the intensity of the reflected light focussed on each diode of the photodiode array, each switch is closed and then opened in succession. When a switch is in the closed position, its capacitor is charged from the line voltage which is represented by the letter "V" in FIG. 6. The capacitor is charged from this voltage "V" through the corresponding switch and through the common load resistance L connected to the output terminal 89 as illustrated in FIG. 6. When the switch again opens the reflected light falling on the photodiode causes a current to flow as indicated by the arrows in FIG. 6. This current discharges the corresponding capacitor by an amount related to the product of the quantity of the reflected light and the length of time that the reflected light falls on the corresponding photodiode. Each time a switch closes, the corresponding capacitor is charged again. At this time a voltage spike is developed across the load resistor L which is proportional to the amount the capacitor has discharged, and thus proportional to the amount of light the photodiode received since the switch closed the previous time.

Figure 7:
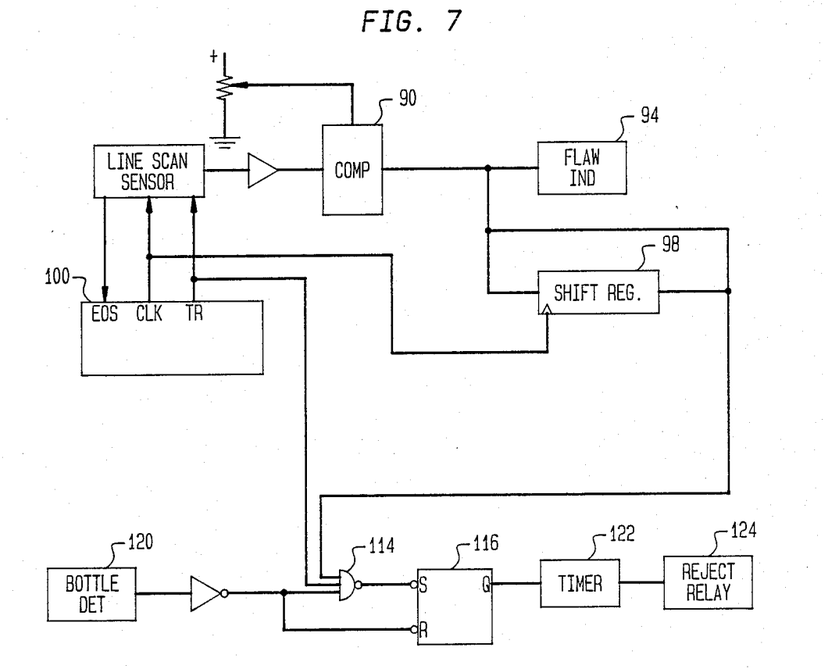
FIG. 7 is an electrical block diagram diagrammatically illustrating an example of a container tracking and reject system in an apparatus according to the present invention.

Referring now to FIG. 7, the signal from the output terminal 89 is amplified and provided to a suitable comparator 90 which compares it to a predetermined threshold value, such as user adjustable reference, to determine if the intensity of the reflected light exceeds the threshold value, and thereby indicate a defect. More particularly, for each photodiode in the line scan camera whose output exceeds the reference value, the comparator 90 produces a pulse. This pulse actuates a flaw indicator 94 and is applied to a recirculating shift register 98. This register is used to track the location of a container having a defect as it continues through the inspection zone. During successive scans of the photodiode array, the pulses are advanced through the shift register. When a pulse is present in the last stage of the shift register at the end of a scan, it is applied to one input terminal of a NAND gate 114 that receives the start signal TR from a line scan control circuit 100 at another of its input terminals. When activated by a defect pulse and the start signal, the NAND gate 114 sets a flip-flop 116 to produce a reject signal.

Referring to FIGS. 1 and 7, a detector 120 senses each container 12 as it leaves the inspection zone 30. This detector can be of any suitable type, such as a light emitting diode which sends a beam of light toward the container and a photodetector which senses light reflected by the container. The output signal from the detector 120 is applied to the reset terminal of the flip-flop 116. This signal is also applied to another input terminal of the gate 114 to prevent the possibility of set and reset signals being applied to the flip-flop 116 at the same time. The resetting of the flip-flop triggers a timer 122 to actuate a reject relay 124 for an appropriate length of time.

The inspection device 10 desirably also has a means for removing any container 12 found to have a defective condition in response to the reject signal. A container removal apparatus 126 is illustrated in FIG. 1. Typically, an example of such apparatus would be a solenoid air valve having a blow-off nozzle. The solenoid of the reject valve is responsive to the relay 124. Typically, indicator means may also be provided, such as light emitting diodes, in conjunction with the container removal apparatus 126 to indicate that a defect signal is being generated and that the detector 120 has detected the presence of a container 12.

When a defect signal indicates the presence of a defective condition, the resulting energization of the relay 124 actuates the solenoid of the container removal apparatus 126 to provide a blast of compressed air from the nozzle of the apparatus 126 to push the defective container 12 from the conveyor 14 and into a suitable disposal means, such as a chute 128 illustrated in FIG. 1.

As is evident from the foregoing, the present invention provides for the simultaneous tracking and inspection of a plurality of transparent containers 12 as they move through the inspection zone 30. Further, the present invention can provide for the inspection of the entire bottom 38 for the presence of defective conditions, by rotating the container 12 as it moves through the inspection zone 30.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A method for inspecting a transparent container, said container having a bottom and a side wall, comprising the steps of:
    focusing light from a light source into a line of light that extends along the length of the bottom of at least one container to be inspected, said focused light entering said container through the exterior surface of said container bottom,
    detecting the intensity of the light passing through said container side wall, after said focused light has passed through said container bottom and been reflected at least at one predetermined angle, and
    comparing the detected intensity of said reflected light with a predetermined threshold value, said predetermined threshold value providing a measure of the acceptability of said container.

2. The method as claimed in claim 1 further comprising the step of generating a reject signal when said detected intensity exceeds said predetermined threshold value.

3. The method as claimed in claim 1 further comprising the step of rotating said container in an inspection zone through a predetermined number of degrees of rotation to pass said line of light through a corresponding portion of said container bottom to permit inspection of said corresponding portion.

4. The method as claimed in claim 1 further comprising the step of continuously moving said container through the length of an inspection zone.

5. The method as claimed in claim 4 further comprising the step of rotating said container in said inspection zone through a predetermined number of degrees of rotation to pass said line of light through a corresponding portion of said container bottom to permit inspection of said corresponding portion.

6. The method as claimed in claim 1 wherein said line of light enters said container bottom at a preselected angle, said preselected angle being measured from a central plane of said container.

7. The method as claimed in claim 6 wherein said preselected angle is in a range of from about 15 degrees to about 45 degrees.

8. The method as claimed in claim 6 wherein said preselected angle is about 30 degrees.

9. The method as claimed in claim 6 wherein said preselected angle is about 45 degrees.

10. The method as claimed in claim 6 wherein said preselected angle provides optimum reflection of light from a defective condition.

11. The method as claimed in claim 1 said at least one predetermined angle is measured from a plane corresponding to the bottom surface of said container.

12. The method as claimed in claim 11 wherein said predetermined angle is in a range of about 10 degrees to about 40 degrees.

13. The method as claimed in claim 11 wherein said predetermined angle is about 10 degrees.

14. The method as claimed in claim 11 wherein said predetermined angle is about 40 degrees.

15. The method as claimed in claim 1 wherein said predetermined angle is selected to promote receiving maximum light reflection from a defective condition.

16. The method as claimed in claim 15 wherein said linearly extending line of light enters said container bottom exterior surface at a preselected angle, said preselected angle being selected to promote optimum light reflection from a defective condition.

17. The method as claimed in claim 11 wherein said reflected light is detected at a first predetermined angle and a second predetermined angle.

18. The method as claimed in claim 17 wherein said first predetermined angle is about 10 degrees and said second predetermined angle is about 40 degrees.

19. The method as claimed in claim 17 wherein said first predetermined angle is selected to promote receiving maximum light reflection from a first defective condition and said second predetermined angle is selected to promote receiving maximum light reflection from a second defective condition.

20. The method as claimed in claim 1 wherein said linearly extending line of light enters said container bottom exterior surface at a preselected angle, said preselected angle being measured from a central plane of said container perpendicular to a plane related to the bottom surface of said container, said preselected angle being in a range of from about 15 degrees to about 45 degrees to promote optimum light reflection from a defective condition, and wherein said at least one predetermined angle is measured from said plane passing through said inspection zone, said predetermined angle being in a range of from about 10 degrees to about 40 degrees to promote reception of maximum light reflected from a defective condition.

21. An apparatus for inspection of a transparent container, said container having a bottom and a side wall extending from said bottom, comprising means for supporting at least one container, said means for supporting including an inspection zone and being adapted to pass a linearly extending line of light to the bottom of a container positioned in said inspection zone, a light source providing said linearly extending line of light focused on said container bottom, said line of light extending the length of said container bottom and entering said container bottom through its exterior surface, means for detecting the intensity of light passing through said container side wall, after said light has passed through said container bottom and been reflected at least at one predetermined angle, and means for comparing the detected intensity of said reflected light with a predetermined threshold value, said threshold value providing a measure of the acceptability of said container.

22. The apparatus as claimed in claim 21 further comprising:

means for rotating said container in said inspection zone through a predetermined number of degrees of rotation to pass said line of light through a corresponding portion of said container bottom to permit inspection of said corresponding portion.

23. The apparatus as claimed in claim 22 wherein said container is rotated through a range of about 180 degrees to about 360 degrees of rotation to inspect said container bottom.

24. The apparatus as claimed in claim 21 further comprising:

means for moving said container through the length of said inspection zone.

25. The apparatus as claimed in claim 24 further comprising:

means for rotating said container in said inspection zone through a predetermined number of degrees of rotation to pass said line of light through a corresponding portion of said container bottom to permit inspection of said corresponding portion.

26. The apparatus as claimed in claim 21 further comprising:

means for rotating said container in said inspection zone through a predetermined number of degrees of rotation to pass said line of light through a corresponding portion of said container bottom to permit inspection of said corresponding portion, and means for moving said container through the length of said inspection zone, said light source providing said line of light to enter said container bottom exterior surface at a preselected angle, said preselected angle being measured from a substantially vertical plane in said inspection zone.

27. The apparatus as claimed in claim 26 wherein said preselected angle is in a range of from about 15 degrees to about 45 degrees, and said predetermined angle is in a range of about 10 degrees to about 40 degrees relative to a substantially horizontal plane related to the bottom of said container.

28. The apparatus as claimed in claim 26 wherein said means for detecting the intensity of light detects said reflected light at a first predetermined angle and a second predetermined angle.

29. The apparatus as claimed in claim 28 wherein said first predetermined angle is about 10 degrees and said second predetermined angle is about 40 degrees.

30. The apparatus as claimed in claim 28 wherein said first predetermined angle is selected to promote receiving maximum light reflection from a first defective condition and said second predetermined angle is selected to promote receiving maximum light reflection from a second defective condition.

31. The apparatus as claimed in claim 26 wherein said preselected angle is selected to promote optimum light reflection from a defective condition, and wherein said predetermined angle is selected to promote receiving maximum light reflection from a defective condition.

32. The apparatus as claimed in claim 21 wherein said predetermined angle is in a range of about 10 degrees to about 40 degrees relative to a plane defined by the bottom of said container.

33. The apparatus as claimed in claim 32 wherein said predetermined angle is selected to promote receiving maximum light reflection from a defective condition.

34. The apparatus as claimed in claim 32 wherein said means for detecting the intensity of light detects said reflected light at a first predetermined angle and a second predetermined angle.

35. The apparatus as claimed in claim 21 further comprising:
means for generating a reject signal when said detected intensity exceeds said predetermined threshold value.

36. The apparatus as claimed in claim 35 further comprising:
means for determining the presence of said container as it leaves said inspection zone, and
means for removing said container in response to said reject signal and said determining means.

37. The apparatus as claimed in claim 21 wherein said means for detecting the intensity of said reflected light includes a line scan camera.

38. A method of inspecting the bottoms of transparent containers for defects, comprising the steps of:
continuously transporting a plurality of transparent containers along a linear path;
focusing light from a source into a line of light which is co-extensive with said linear path so that said containers travel along said line of light, said light being directed at the bottoms of the containers to enter the containers from the exterior surfaces thereof;
rotating said containers as they travel along said linear path so that the line of light scans the bottom exterior surfaces of the containers; and
detecting the intensity of light which is reflected at the bottoms of the containers and exits the containers through the side wall thereof at a predetermined angle.

39. The method of claim 38 wherein said predetermined angle is in the range of about 10 degrees to about 40 degrees relative to the bottom surfaces of the containers.

40. The method of claim 38 wherein said light is directed at the bottom exterior surfaces of said containers at an angle in the range of about 15 degrees to about 45 degrees relative to the central axes of said containers.

* * * * *